US011118312B2

(12) United States Patent
Behabtu et al.

(10) Patent No.: US 11,118,312 B2
(45) Date of Patent: *Sep. 14, 2021

(54) POLY ALPHA-1,3-GLUCAN FIBRIDS AND USES THEREOF AND PROCESSES TO MAKE POLY ALPHA-1,3-GLUCAN FIBRIDS

(71) Applicant: NUTRITION & BIOSCIENCES USA 4, INC., Rochester, NY (US)

(72) Inventors: Natnael Behabtu, Leiden (NL); Jayme L. Paullin, Exton, PA (US); Mikhail R. Levit, Glen Allen, VA (US)

(73) Assignee: NUTRITION & BIOSCIENCES USA 4, INC., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/572,257

(22) PCT Filed: May 19, 2016

(86) PCT No.: PCT/US2016/033249
§ 371 (c)(1),
(2) Date: Nov. 7, 2017

(87) PCT Pub. No.: WO2016/196022
PCT Pub. Date: Dec. 8, 2016

(65) Prior Publication Data
US 2018/0119357 A1    May 3, 2018

Related U.S. Application Data

(60) Provisional application No. 62/169,086, filed on Jun. 1, 2015.

(51) Int. Cl.
| | | |
|---|---|---|
| *D21H 13/30* | (2006.01) | |
| *D21H 13/20* | (2006.01) | |
| *D21H 27/10* | (2006.01) | |
| *H01B 3/52* | (2006.01) | |
| *C08B 37/00* | (2006.01) | |
| *C08L 5/00* | (2006.01) | |
| *C09K 8/588* | (2006.01) | |
| *C12P 19/04* | (2006.01) | |
| *C12P 19/18* | (2006.01) | |

(52) U.S. Cl.
CPC ......... *D21H 13/30* (2013.01); *C08B 37/0009* (2013.01); *C08L 5/00* (2013.01); *C09K 8/588* (2013.01); *C12P 19/04* (2013.01); *C12P 19/18* (2013.01); *D21H 13/20* (2013.01); *D21H 27/10* (2013.01); *H01B 3/52* (2013.01); *C09K 2208/08* (2013.01)

(58) Field of Classification Search
CPC .......... D21H 13/20; D21H 13/30; D21H 5/20; C09K 2208/08; C08L 2203/12; C08L 2205/16; C08B 37/0009; C12P 19/18; C12P 19/04; D01D 5/06; D01D 5/04; D01D 5/11; D01F 9/00; D01F 11/00; C09D 105/00; Y10S 264/08

See application file for complete search history.

(56) References Cited

U.S. PATENT DOCUMENTS

| | | | | |
|---|---|---|---|---|
| 2,708,617 A | * | 5/1955 | Magat | B29D 7/01 264/184 |
| 2,999,788 A | * | 9/1961 | Winthrop | D01D 5/04 162/146 |
| 5,702,942 A | | 12/1997 | Leathers et al. | |
| 6,127,602 A | * | 10/2000 | Nichols | C12N 9/1051 435/101 |
| 6,284,479 B1 | * | 9/2001 | Nichols | C07H 1/00 162/100 |
| 7,000,000 B1 | * | 2/2006 | O'Brien | C12P 19/08 536/123.12 |
| 8,197,641 B2 | | 6/2012 | Esser et al. | |
| 8,827,192 B2 | * | 9/2014 | Innerlohinger | C08K 3/22 241/21 |
| 9,822,188 B2 | | 11/2017 | Manner et al. | |
| 9,957,334 B2 | | 5/2018 | Dennes et al. | |
| 2001/0024716 A1 | * | 9/2001 | Chen | D04H 1/68 428/317.9 |
| 2003/0220039 A1 | * | 11/2003 | Chen | D04H 1/68 442/327 |
| 2006/0127328 A1 | | 6/2006 | Monsan et al. | |
| 2011/0028608 A1 | * | 2/2011 | Innerlohinger | C08L 1/02 524/35 |
| 2012/0132381 A1 | | 5/2012 | Hentze et al. | |
| 2012/0318169 A1 | | 12/2012 | Schuster et al. | |
| 2013/0244287 A1 | | 9/2013 | O'Brien et al. | |
| 2013/0244288 A1 | | 9/2013 | O'Brien et al. | |
| 2014/0318415 A1 | * | 10/2014 | Innerlohinger | C08L 101/00 106/447 |

(Continued)

FOREIGN PATENT DOCUMENTS

| | | | | |
|---|---|---|---|---|
| CA | 2003221 A1 | | 5/1990 | |
| CA | 2985685 A1 | * | 12/2016 | C08B 37/0009 |

(Continued)

OTHER PUBLICATIONS

Machine Translation of WO 20144/161019 A1 (Year: 2014).*

(Continued)

*Primary Examiner* — Jose A Fortuna

(57) ABSTRACT

Disclosed herein are poly alpha-1,3-glucan fibrids and methods for making them. The fibrids have a fibrous shape with an average length of between 10 μm and 10 mm and width of between 200 nm and 200 μm. Also disclosed are uses for the fibrids, including paper-making and as a viscosity modifier in making formulations for applications such as laundry applications and personal care applications, and as an emulsifier in food.

23 Claims, 6 Drawing Sheets

(56) References Cited

U.S. PATENT DOCUMENTS

| | | | |
|---|---|---|---|
| 2015/0232785 A1* | 8/2015 | Paullin | C11D 3/0036 |
| | | | 510/299 |
| 2016/0230348 A1 | 8/2016 | Massouda | |
| 2016/0311935 A1* | 10/2016 | Dennes | C11D 17/0008 |
| 2016/0348280 A1 | 12/2016 | Schuster et al. | |
| 2018/0119357 A1* | 5/2018 | Behabtu | C08B 37/0009 |
| 2018/0127682 A1* | 5/2018 | Nambiar | A61Q 5/02 |
| 2019/0186049 A1* | 6/2019 | Durnberger | D01F 2/24 |
| 2019/0330802 A1* | 10/2019 | Behabtu | D21H 17/17 |
| 2020/0002646 A1* | 1/2020 | Huang | C11D 3/0036 |
| 2020/0062929 A1* | 2/2020 | Behabtu | C08L 1/02 |
| 2020/0062931 A1* | 2/2020 | Behabtu | C08B 37/0018 |
| 2020/0131281 A1* | 4/2020 | Guan | C12P 19/04 |
| 2020/0190270 A1* | 6/2020 | Behabtu | C08K 5/09 |
| 2020/0370216 A1* | 11/2020 | Behabtu | C08L 51/02 |
| 2021/0130504 A1* | 5/2021 | Kim | C09D 7/65 |

FOREIGN PATENT DOCUMENTS

| | | | |
|---|---|---|---|
| CA | 2985685 A1 | 12/2016 | |
| EP | 0824105 A2 | 2/1998 | |
| EP | 0824106 A2 | 2/1998 | |
| EP | 0824107 A2 | 2/1998 | |
| EP | 3303697 B1 | 4/2018 | |
| WO | 2013101854 A1 | 7/2013 | |
| WO | WO-2013101854 A1 * | 7/2013 | |
| WO | 2014161019 A1 | 10/2014 | |
| WO | WO-2014161018 A1 * | 10/2014 | D04H 1/28 |
| WO | WO-2014161019 A1 * | 10/2014 | D01F 9/00 |
| WO | WO-2014201481 A1 * | 12/2014 | B29C 48/022 |
| WO | 2015069828 A1 | 5/2015 | |
| WO | 2015123323 A1 | 5/2015 | |
| WO | WO-2015069828 A1 * | 5/2015 | C08K 5/09 |
| WO | WO-2015095358 A1 * | 6/2015 | C11D 17/0008 |
| WO | 2015130883 A9 | 9/2015 | |
| WO | WO-2015130883 A1 * | 9/2015 | C12P 19/16 |
| WO | 2015183724 A1 | 12/2015 | |
| WO | WO-2015183724 A1 * | 12/2015 | A23L 5/00 |
| WO | WO-2016123644 A1 * | 8/2016 | C08L 5/00 |
| WO | 2016196021 A1 | 12/2016 | |
| WO | 2016196022 A1 | 12/2016 | |
| WO | WO-2016196021 A1 * | 12/2016 | A61Q 5/02 |
| WO | WO-2016196022 A1 * | 12/2016 | C08B 37/0009 |
| WO | WO-2017079595 A1 * | 5/2017 | C08L 5/00 |
| WO | WO-2019005927 A1 * | 1/2019 | C08J 3/22 |
| WO | WO-2019055397 A1 * | 3/2019 | C08L 5/02 |

OTHER PUBLICATIONS

Simpson et al., Microbiology, (1995), vol. 141, pp. 1451-1460.
Ogawa, Fiber Differentiation Methods, (1980), vol. 47, pp. 353-362.
Smoukov et al., Adv. Mater., (2015), vol. 27, pp. 2642-2647.
International Preliminary Report on Patentability, PCT/US2016/033249, dated May 12, 2017.
Behabtu et al., Enzymatic Polymerization Routes to Synthetic-Natural Materials: A Review, ACS Sustainable Chem. Eng., vol. 8, pp. 9947-9954 (2020).

* cited by examiner

POLY ALPHA-1,3-GLUCAN FIBRIDS AND USES THEREOF AND PROCESSES TO MAKE POLY ALPHA-1,3-GLUCAN FIBRIDS

CROSS-REFERENCE TO RELATED APPLICATIONS

This application claims priority under 35 USC § 371 as a national phase of International Patent Application No. PCT/US2016/033249 (filed May 19, 2016; and published on Dec. 8, 2016 as Publication No. WO 2016/196022 A1), which claims priority to and the benefit of U.S. provisional patent application No. 62/169,086, filed Jun. 1, 2015, the entirety of which is herein incorporated by reference.

FIELD OF INVENTION

This invention is in the field of polysaccharide fibrids. Specifically, this invention pertains to novel poly alpha-1,3-glucan fibrids, compositions containing them, and processes to produce such fibrids.

BACKGROUND

Driven by a desire to find new structural polysaccharides using enzymatic syntheses or genetic engineering of microorganisms or plant hosts, researchers have discovered polysaccharides that are biodegradable, and that can be made economically from renewable resource-based feedstocks. One such polysaccharide is poly alpha-1,3-glucan, a glucan polymer characterized by having alpha-1,3-glycosidic linkages.

This polymer has been isolated by contacting an aqueous solution of sucrose with a glucosyltransferase enzyme isolated from *Streptococcus salivarius* (Simpson et al., *Microbiology* 141:1451-1460, 1995). Films prepared from poly alpha-1,3-glucan tolerate temperatures up to 150° C. and provide an advantage over polymers obtained from beta-1,4-linked polysaccharides (Ogawa et al., *Fiber Differentiation Methods* 47:353-362, 1980).

U.S. Pat. No. 7,000,000 disclosed the preparation of a polysaccharide fiber comprising hexose units, wherein at least 50% of the hexose units within the polymer were linked via alpha-1,3-glycosidic linkages using an *S. salivarius* gtfJ enzyme. This enzyme utilizes sucrose as a substrate in a polymerization reaction producing poly alpha-1,3-glucan and fructose as end-products (Simpson et al., 1995).

U.S. Pat. No. 6,284,479, issued to Nichols on Sep. 4, 2001, discloses methods of making/coating paper, utilizing "non-fibrillated" glucans produced by glucosyltransferases B, C or D enzyme of the species *Streptococcus mutans*, instead of modified starches. The term "glucan" is defined therein as a glucose polymer having linkages that are predominantly (1,3), (1,6) with branch points occurring at (1,3,6). Minor linkages at (1,2) and (1,4).

U.S. Pat. No. 6,127,602 issued to Nichols on Oct. 3, 2000, discloses transgenic plant cells containing a DNA from *Streptococcus mutans*, and encoding the glucosyltransferase B enzyme or an enzymatically active fragment thereof. It is disclosed that the "non-fibrillated" glucan produced from this enzyme is functionally similar to modified starch used in paper manufacture. It was also noted that the glucans also exhibited similar physical properties to thermoplastic molecules used in the coating step during paper manufacture.

U.S. Pat. No. 2,999,788, issued to Morgan on Sep. 12, 1961, discloses a non-rigid, wholly synthetic polymeric material, referred to as a "fibrid", which is useful in the production of sheet-like structures such a paper.

Smoukov et al., Adv. Mater. 2015, 27, 2642-2647, describe a scalable liquid shear-driven fabrication of polymer nanofibers. The shear precipitation process takes place during direct injection of polymer solutions in the bulk of a viscous medium under shear. The polymer solvent is miscible with the shearing medium. A polymer antisolvent is mixed with the shear medium which induces precipitation of the injected dissolved polymer. Nanofibers are made that are dispersed and carried in a flux of liquid. It also described how controlling the polymer and antisolvent concentrations allows formation of nanofibers with uniform diameter in the nanoscale range.

Since glucan polymer can be used in a variety of applications, the ability to dissolve the polymer is very important.

A variety of fillers can be used in the paper-making industry. One of the most common and least expensive filler is calcium carbonate. A drawback with the use of large amounts of calcium carbonate is that with increasing amounts, the mechanical strength of the paper decreases and the recyclability of highly filled paper also decreases. Therefore, there exists a need for a filler that can help to increase paper strength with increasing amounts of filler and retain good recyclability with the increased filler amounts.

SUMMARY OF INVENTION

In one embodiment, fibrids comprising poly alpha-1,3-glucan are disclosed. The fibrids have a fibrous shape with an average length of between 10 µm and 10 mm and width of between 200 nm and 200 µm.

In a second embodiment, a process for making fibrids comprising precipitating poly alpha-1,3-glucan under shear in a non-solvent to produce a suspension comprising fibrids is disclosed.

This process can be used to alter at least one of (i) viscosity of the suspension containing the fibrids, (ii) size of the fibrids, or (iii) shape of the fibrids by controlling at least one process parameter wherein the process parameter is dope concentration, type of mixer, mixing speed, pH of precipitation bath, rate of addition of solvent in which poly alpha-(1,3)-glucan is dissolved, amount of non-solvent used, duration of mixing, rate of neutralization, and/or concentration of neutralizer.

In a third embodiment is disclosed a process for making fibrids comprising:

(a) dissolving poly alpha-1,3-glucan in a solvent to make a poly alpha-1,3-glucan solution;

(b) precipitating poly alpha-1,3-glucan fibrids under shear to produce a suspension containing the fibrids;

In another aspect, the fibrid-containing suspension of step (b) can be filtered to isolate the fibrids and, optionally, the fibrids can be dried.

In still another aspect, the process can include at least one of the following:

(a) the solvent can be an aqueous basic solution; and (b) the precipitation bath comprises at least one of an aqueous acidic solution, an aqueous alkali solution, and/or an alcohol.

In another embodiment, a paper is disclosed comprising:

(a) poly alpha-1,3-glucan fibrids; and (b) optionally, wood pulp.

This paper can be in the form of a packaging material, or an insulating material.

Also disclosed is a process for making a paper of poly alpha-1,3-glucan fibrids and, optionally, wood pulp comprising:

(a) dispersing the poly alpha-1,3-glucan fibrids of claim 1, optionally, with wood pulp in an aqueous medium to form a slurry; and (b) forming a paper from the slurry by filtering off the aqueous medium to form a wet paper and drying the wet paper.

This process can further comprise:

(c) calendering the paper.

In another aspect viscosity modifiers and emulsifiers comprising poly alpha-1,3-glucan fibrids of the invention are disclosed. Use of these fibrids in personal care, food or enhanced oil recovery applications are still another embodiment of the invention.

DETAILED DESCRIPTION OF INVENTION

Figure 1A:
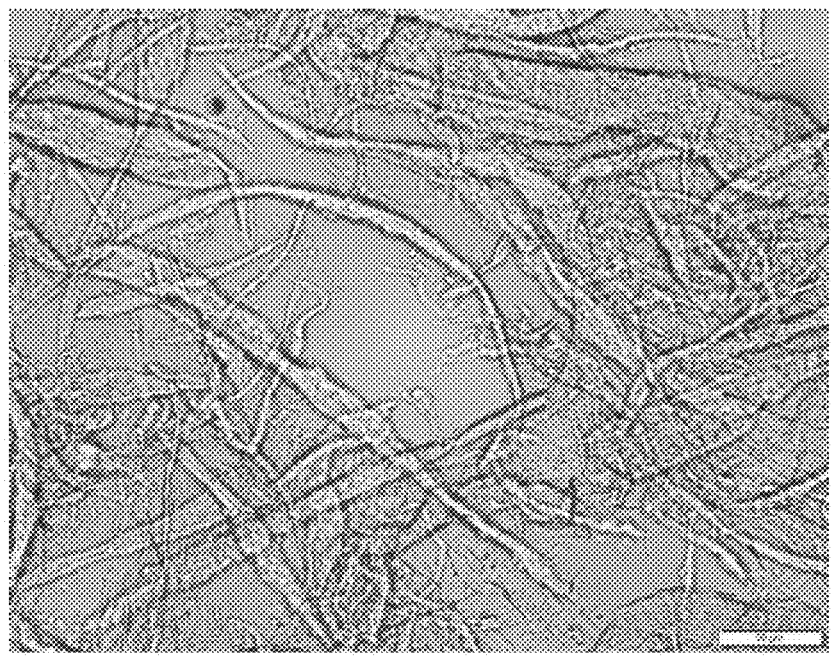
FIGS. 1a and 1b are microscopy images of the same spot showing fibrid structure.

The disclosures of all patent and non-patent literature cited herein are incorporated herein by reference in their entirety.

As used herein, the term "invention" or "disclosed invention" is not meant to be limiting, but applies generally to any of the inventions defined in the claims or described herein. These terms are used interchangeably herein.

As used herein, the term "colloidal dispersion" refers to a heterogeneous system having a dispersed phase and a dispersion medium, i.e., microscopically dispersed insoluble particles are suspended throughout another substance. The stability of a colloidal system is defined by particles remaining suspended in solution at equilibrium. A dispersed phase comprising very small particles dispersed in a continuous liquid medium can be collectively referred to as a sol. The particles are too tiny to be seen with the unaided eye (typically 10 nm to 100 μm or even 200 μm), but are larger than single atoms and ordinary single molecules. An example of a colloidal dispersion in water is a hydrocolloid.

The term "suspension" as used herein refers to the state of a substance when its particles are mixed with but undissolved in a fluid or solid.

The terms "poly alpha-1,3-glucan", "alpha-1,3-glucan polymer" and "glucan polymer" are used interchangeably herein. Poly alpha-1,3-glucan is a polymer comprising glucose monomeric units linked together by glycosidic linkages, wherein at least 50% of the glycosidic linkages are alpha-1,3-glycosidic linkages. Poly alpha-1,3-glucan is a type of polysaccharide. The structure of poly alpha-1,3-glucan can be illustrated as follows:

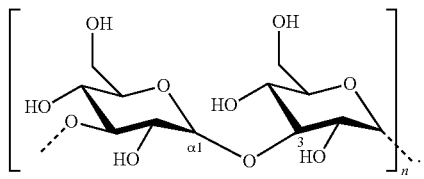

Poly alpha-1,3-glucan can be prepared using chemical methods. Alternatively, it can be prepared by extracting it from various organisms, such as fungi, that produce poly alpha-1,3-glucan. Alternatively, still, poly alpha-1,3-glucan can be enzymatically produced from sucrose using one or more glucosyltransferase (gtf) enzymes (e.g., gtfJ), such as described in U.S. Pat. No. 7,000,000, and U.S. Patent Appl. Publ. Nos. 2013/0244288 and 2013/0244287 (all of which are incorporated herein by reference), for example.

The terms "poly alpha-1,3-1,6-glucan", "alpha-1,3-1,6-glucan polymer", and "poly (alpha-1,3)(alpha-1,6) glucan" are used interchangeably herein (note that the order of the linkage denotations "1,3" and "1,6" in these terms is of no moment). Poly alpha-1,3-1,6-glucan herein is a polymer comprising glucose monomeric units linked together by glycosidic linkages (i.e., glucosidic linkages), wherein at least 30% of the glycosidic linkages are alpha-1,3-glycosidic linkages, and at least 30% of the glycosidic linkages are alpha-1,6-glycosidic linkages. Poly alpha-1,3-1,6-glucan is a type of polysaccharide containing a mixed glycosidic linkage content. The meaning of the term poly alpha-1,3-1,6-glucan in certain embodiments herein excludes "alternan," which is a glucan containing alpha-1,3 linkages and alpha-1,6 linkages that consecutively alternate with each other (U.S. Pat. No. 5,702,942, U.S. Pat. Appl. Publ. No. 2006/0127328). Alpha-1,3 and alpha-1,6 linkages that "consecutively alternate" with each other can be visually represented by . . . G-1,3-G-1,6-G-1,3-G-1,6-G-1,3-G-1,6-G-1,3-G-. . . , for example, where G represents glucose.

At least 50%, 60%, 70%, 80%, 90%, 95%, 96%, 97%, 98%, 99%, or 100% (or any integer value between 50% and 100%) of glycosidic linkages between the glucose monomer units of poly alpha-1,3-glucan used to prepare poly alpha-1,3-glucan compounds herein are alpha-1,3. In such embodiments, accordingly, poly alpha-1,3-glucan has less than 50%, 40%, 30%, 20%, 10%, 5%, 4%, 3%, 2%, 1%, or 0% (or any integer value between 0% and 50%) of glycosidic linkages that are not alpha-1,3.

The terms "glycosidic linkage" and "glycosidic bond" are used interchangeably herein and refer to the type of covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. This linkage is illustrated in the poly alpha-1,3-glucan structure provided above. Herein, "alpha-D-glucose" will be referred to as "glucose".

The term "poly alpha-1,3-glucan slurry" herein refers to an aqueous mixture comprising the components of a glucosyltransferase enzymatic reaction such as poly alpha-1,3-glucan, sucrose, one or more glucosyltransferase enzymes, glucose and fructose.

The term "poly alpha-1,3-glucan wet cake" herein refers to poly alpha-1,3-glucan that has been separated from a slurry and washed with water or an aqueous solution. Poly alpha-1,3-glucan is not dried when preparing a wet cake.

The term "viscosity" as used herein refers to the measure of the extent to which a fluid or an aqueous composition such as a hydrocolloid resists a force tending to cause it to flow. Various units of viscosity that can be used herein include centipoise (cPs) and Pascal-second (Pa·s). A centipoise is one one-hundredth of a poise; one poise is equal to 0.100 kg·m$^{-1}$·s$^{-1}$. Thus, the terms "viscosity modifier" and "viscosity-modifying agent" as used herein refer to anything that can alter/modify the viscosity of a fluid or aqueous composition.

The term "shear thinning behavior" as used herein refers to a decrease in the viscosity of the colloidal dispersion as shear rate increases. The term "shear thickening behavior" as used herein refers to an increase in the viscosity of the colloidal dispersion as shear rate increases. "Shear rate" herein refers to the rate at which a progressive shearing deformation is applied to the colloidal dispersion. A shearing deformation can be applied rotationally.

The "molecular weight" of the poly alpha-1,3-glucan and poly alpha-1,3-glucan compounds herein can be represented as number-average molecular weight ($M_n$) or as weight-average molecular weight ($M_w$). Alternatively, molecular weight can be represented as Daltons, grams/mole, DPw (weight average degree of polymerization), or DPn (number average degree of polymerization). Various means are known in the art for calculating these molecular weight measurements, such as high-pressure liquid chromatography (HPLC), size exclusion chromatography (SEC), or gel permeation chromatography (GPC).

The terms "percent by volume", "volume percent", "vol %" and "v/v %" are used interchangeably herein. The percent by volume of a solute in a solution can be determined using the formula: [(volume of solute)/(volume of solution)]×100%.

The terms "percent by weight (% by wt.)", "weight percentage (wt %)" and "weight-weight percentage (% w/w)" are used interchangeably herein. Percent by weight refers to the percentage of a material on a mass basis as it is comprised in a composition, mixture or solution.

Viscosity can be measured with the colloidal dispersion at any temperature between 3° C. to 110° C. (or any integer between 3 and 110° C.). Alternatively, viscosity can be measured at a temperature between 4° C. to 30° C., or 20° C. to 25° C. Viscosity can be measured at atmospheric pressure (about 760 torr) or any other higher or lower pressure.

Viscosity Index ("VI"'s) is an arbitrary measure for the change in viscosity with variations in temperature.

The viscosity of a colloidal dispersion disclosed herein can be measured using a viscometer or rheometer, or using any other means known in the art. It would be understood by those skilled in the art that a rheometer can be used to measure the viscosity of those hydrocolloids and aqueous solutions of the invention that exhibit shear thinning behavior or shear thickening behavior (i.e., liquids with viscosities that vary with flow conditions). The viscosity of such embodiments can be measured at a rotational shear rate of 10 to 1000 rpm (revolutions per minute) (or any integer between 10 and 1000 rpm), for example. Alternatively, viscosity can be measured at a rotational shear rate of 10, 60, 150, 250, or 600 rpm.

The terms "viscosity modifier" and "viscosity index improver" can be used interchangeably herein. The terms refer to polymeric molecules that are sensitive to temperature. Such viscosity modifiers can be added to influence the viscosity-temperature relationship of a fluid.

The pH of a colloidal dispersion disclosed herein can be between 2.0 to 12.0. Alternatively, pH can be 2.0, 3.0, 4.0, 5.0, 6.0, 7.0, 8.0, 9.0, 10.0, 11.0, 12.0; or between 4.0 to 8.0; or between 3.0 and 11.0. In certain embodiments, the viscosity of the colloidal dispersion does not largely fluctuate at a pH between 3.0 and 11.0.

A poly alpha-1,3-glucan compound disclosed herein can be present in a colloidal dispersion at a weight percentage (wt %) of at least 0.01%, 0.05%, 0.1%, 0.2%, 0.3%, 0.4%, 0.5%, 0.6%, 0.7%, 0.8%, 0.9%, 1.0%, 1.2%, 1.4%, 1.6%, 1.8%, 2.0%, 2.5%, 3.0%, 3.5%, 4.0%, 4.5%, 5%, 6%, 7%, 8%, 9%, 10%, 11%, 12%, 13%, 14% or 15%.

The term "fibrids", as used herein, means nongranular, fibrous or film-like particles with at least one of their three dimensions being of minor magnitude relative to the largest dimension. In some embodiments, the poly alpha-1,3-glucan can have a fiber-like and/or a sheet-like structure with a relatively large surface area when compared to a fiber. The surface area can be in the range of 5 to 50 meter$^2$/gram of material, with the largest dimension particle size of about 10 to 1000 micrometers and the smallest dimension size, length or thickness of 0.05 to 0.25 micrometers, resulting in an aspect ratio of largest to smallest dimension of 40 to 20,000. The terms "fibrids", "poly alpha-1,3-glucan fibrids" and "fibrillated glucan" are used interchangeably herein.

These fibrids can be prepared by precipitation of a solution of polymeric material such as poly alpha-1,3-glucan using a non-solvent under shear, preferably, high shear. The term "non-solvent" as used herein means that it is a poor solvent for the polymeric material, for example, the polymeric material has a solubility of less than 5 wt % in the solvent. In other embodiments, the polymeric material can have a solubility of less than 4, 3, 2, 1 or 0.5 wt % in the solvent. Examples of suitable non-solvents for the poly alpha-1,3-glucan include, for example, methanol, ethanol, isopropanol, acetone, aqueous acidic solution, water, etc.

In some embodiments, the process for making the fibrids comprises:
(a) dissolving poly alpha-1,3-glucan in a solvent to make a poly alpha-1,3-glucan solution;
(b) precipitating poly alpha-1,3-glucan fibrids under shear to produce a suspension containing the fibrids.

Fibrids of the invention can be made by the addition of a poly alpha-1,3-glucan solution into a precipitating bath of liquid ("non-solvent"). The addition of the poly alpha-1,3-glucan solution into the precipitating bath can be accomplished using any standards methods known to those skilled in the art. For example, direct injection can be used.

During the addition, the stream of polymer solution is subjected to shearing forces and turbulence causing the fibrids to precipitate in the form of a suspension by using a non-solvent (i.e., a liquid that has a solubility for the poly alpha-1,3-glucan of less than 5 wt %), in other words, that is immiscible with poly alpha-1,3-glucan. In some embodiments, the precipitating bath can comprise acid or alkali aqueous solution or alcohol.

It is possible to control (i) the viscosity of the suspension containing fibrids (ii) the size and/or (iii) the shape of the fibrids by controlling one or more process parameters such as, for example, the dope concentration, the type of solvent, the type of mixer, the mixing speed, the pH of precipitation bath, the rate of addition of the solution containing polymer, the amount of non-solvent used, the duration of mixing, the neutralization rate and the concentration of neutralizer.

The term "dope" as used herein refers to solution containing polymer. A dope can be prepared by mixing polymer into a solvent. Thus, as well known to those skilled in the art, dope concentration refers to the amount of polymer mixed into the solvent.

The fibrids can be isolated by filtering the suspension. Optionally, the isolated fibrids can be washed with water and/or dried. It is believed that it is possible to resuspend the dried fibrids either by adding a component such as carboxymethyl cellulose and the like or by functionalizing the fibrids by adding certain groups that would facilitate resuspension in a liquid.

Types of solvent for the poly alpha-1,3-glucan that can be used to practice the process of the invention include, but are not limited to, an aqueous basic solution containing components such as sodium hydroxide, potassium hydroxide, lithium hydroxide, lithium chloride/DMAC, DMSO/lithium chloride, etc. The solvent for the poly alpha-1,3-glucan should be miscible with the liquid used for the precipitation bath.

Any type of mixer can be used to practice the invention. For example, a Waring blender can be used. The mixing speed and the duration of mixing can be adjusted as desired.

The pH of the precipitation bath can be adjusted from acidic to neutral to basic depending upon the solvent chosen in which to mix the poly alpha-1,3-glucan. In other embodiments, the amount of non-solvent as well as the rate at which the solution of poly alpha-1,3-glucan is added to the non-solvent can also be varied.

In some embodiments, the rate of neutralization and amount of neutralizer used can also be adjusted. The term "neutralization" means the process of making a solution neutral by adding a base to an acidic solution or adding acid to a basic solution. The term "neutralizer" means any agent that increases the pH of an acidic solution or decreases the pH of a basic solution.

Fibrids disclosed herein can be used in a variety of applications such as paper making/coating (particularly in the wet end of the paper making process), and can be used as a viscosity modifier in making formulations for a variety of applications. These applications include, but are not limited to, laundry applications, personal care applications, food, e.g., food emulsification, in the oil and gas industry and in making composites.

Personal care products may be in the form of, for example, lotions, creams, pastes, balms, ointments, pomades, gels, liquids, combinations of these and the like. There can also be mentioned makeup, lipstick, mascara, rouge, foundation, blush, eyeliner, lip liner, lip gloss, other cosmetics, sunscreen, sun block, nail polish, mousse, hair spray, styling gel, nail conditioner, bath gel, shower gel, body wash, face wash, shampoo, hair conditioner (leave-in or rinse out), cream rinse, hair dye, hair coloring product, hair shine product, hair serum, hair anti-frizz product, hair split-end repair product, lip balm, skin conditioner, cold cream, moisturizer, body spray, soap, body scrub, exfoliant, astringent, scuffing lotion, depilatory, permanent waving solution, antidandruff formulation, antiperspirant composition, deodorant, shaving product, pre-shaving product, aftershaving product, cleanser, skin gel, rinse, dentifrice composition, toothpaste, mouthwash, etc.

Food emulsifiers act as an interface between various components of food, for example, water and oil. While preparing food, immiscible components of food are combined. It can be difficult to produce a stable emulsion when both oil and water components are present in the foodstuff. Each component of food (carbohydrate, protein, oil and fat, water, air, etc.) has its own properties which are sometimes immiscible to one another just like oil and water. To make the two components compatible, emulsifiers are often used.

Several types of emulsifiers can be used in industry, including use in foods, pharmaceuticals, cosmetics and pigments. In some applications, a surfactant-type emulsifier is used wherein the emulsifier is a molecule with a lipophilic portion and hydrophilic portion in one molecule. The lipophilic end of the emulsifier surrounds droplets of the oil component stabilizing the oil in the aqueous phase. One example of a naturally occurring emulsion is milk, which is a complex mixture of fat suspended in an aqueous solution. Other types of emulsifiers stabilize the mixture of oil and water by increasing the viscosity of the aqueous component. Fibrids of poly alpha-1,3-glucan can help to stabilize water and oil compositions by increasing the viscosity of the aqueous components.

As was mentioned above, is believed that poly alpha-1,3-glucan fibrids of the invention may have applicability in the oil and gas industry where increased viscosity is desired. For example, such fibrids may have usefulness in enhanced oil recovery. Abbreviated "EOR", enhanced oil recovery is the implementation of various techniques for increasing the amount of crude oil that can be extracted from an oil field. EOR is also called improved oil discovery or tertiary recovery.

There are three primary techniques of EOR: gas injection, thermal injection and chemical injection. Gas injection, which uses gases such as natural gas, nitrogen or carbon dioxide, accounts for nearly 60% of EOR production in the United States. Thermal injection, which involves the introduction of heat, accounts for nearly 40% of EOR production in the United States. Chemical injection, which can involve the use of long-chained molecules such as polymers, to increase the effectiveness of waterfloods, accounts for about one percent of EOR production in the United States.

Injection of a dilute solution of polymer, which may or may not be water soluble, to increase the viscosity of the injected water can increase the amount of oil recovered in some formations.

Paper can be made from the poly alpha-1,3-glucan fibrids disclosed herein by mixing the fibrids with wood pulp. The resulting paper disclosed herein can be formed on equipment of any scale, from laboratory screens to commercial-sized papermaking machinery, including such commonly used machines as Fourdrinier or inclined wire paper machines. A typical process involves making a dispersion of fibrids and the pulp in an aqueous liquid, draining the liquid from the dispersion to yield a wet composition and drying the wet paper composition. The concentration of fibrids and pulp in the dispersion can range from 0.01 to 3.0 weight percent based on the total weight of the dispersion.

It has also been found that the fibrids of this invention can be used to coat paper. For example, a paper coated with a 100% fibrid coating should have improved barrier properties such as a low oxygen transmission rate and barrier to oil. A pigmented formulation comprising at least one pigment and fibrids of the invention can be used to coat or color the surface of a paper. Relative amounts of each component can be determined by one skilled in the art.

Typically, the aqueous liquid of the dispersion is generally water, but may include various other components such as pH-adjusting components, forming aids, surfactants, defoamers and the like. The aqueous liquid is usually drained from the dispersion by moving the dispersion onto a screen or other perforated support, retaining the dispersed solids and then passing the liquid to yield a wet paper composition. The wet composition, once formed on the support, is usually further dewatered by vacuum or other pressure forces and further dried by evaporating the remaining liquid.

Once the paper is formed, it can be, optionally, calendered. Calendering is a finishing process used on cloth, paper or plastic film. Calendering is used to smooth, coat or thin a material. In paper manufacturing, it produces a smooth, uniform surface more suitable for writing and many printing processes. It also can increase the density and strength of the paper.

Generally, the paper is calendered in the nip between metal-metal, metal-composite, or composite-composite rolls. Also, several nips in the raw can be used, as for example, in the super calendar. Alternatively, the paper can be compressed in a platen press at a pressure, temperature, and time that are optimal for a particular composition and final application. Calendering paper in this manner also decreases the porosity of the formed paper.

The paper can also include inorganic particles and representative particles include titanium dioxide, calcium carbonate, mica, vermiculite, and the like; the addition of these particles can impart properties such as improved printability, appearance, thermal conductivity, dimensional stability, and the like to the paper and the final structures.

The paper of this invention can be used as a packaging material, electrical insulation and in other applications where improved barrier properties and enhanced mechanical performance are desired.

In one embodiment, fibrids comprising poly alpha-1,3-glucan are disclosed. The fibrids have a fibrous shape with an average length of between 10 µm and 10 mm and width of between 200 nm and 200 µm.

In a second embodiment, a process for making fibrids comprising precipitating poly alpha-1,3-glucan under shear in a non-solvent to produce a suspension comprising fibrids is disclosed.

This process can be used to alter at least one of (i) viscosity of the suspension containing the fibrids, (ii) size of the fibrids, or (iii) shape of the fibrids by controlling at least one process parameter wherein the process parameter is the dope concentration, the type of mixer, the mixing speed, the pH of precipitation bath, the rate of addition of solvent in which poly alpha-(1,3)-glucan is dissolved, the amount of non-solvent used, the duration of mixing, the rate of neutralization, and/or the concentration of neutralizer.

In a third embodiment is disclosed a process for making fibrids comprising:
(a) dissolving poly alpha-1,3-glucan in a solvent to make a poly alpha-1,3-glucan solution;
(b) precipitating poly alpha-1,3-glucan fibrids under shear to produce a suspension containing the fibrids;
In another aspect, the fibrid-containing suspension of step can be filtered to isolate the fibrids and, optionally, the fibrids can be dried.
In still another aspect, the process can include at least one of the following:
(a) the solvent can be an aqueous basic solution; and
(b) the precipitation bath wherein the precipitation bath is an aqueous acidic solution, aqueous alkali solution, or an alcohol.

In another embodiment, a paper is disclosed comprising:
(a) poly alpha-1,3-glucan fibrids; and
(b) optionally, wood pulp.
This paper can be in the form of a packaging material, or an insulating material.

Also disclosed is a process for making a paper of poly alpha-1,3-glucan fibrids and, optionally, wood pulp comprising:
(a) dispersing the poly alpha-1,3-glucan fibrids of claim 1, optionally, with wood pulp in an aqueous medium to form a slurry; and
(b) forming a paper from the slurry by filtering off the aqueous medium to form a wet paper and drying the wet paper.
This process can further comprise:
(c) calendering the paper.

In another aspect viscosity modifiers and emulsifiers comprising poly alpha-1,3-glucan fibrids of the invention are disclosed. Use of these fibrids in personal care, food or enhanced oil recovery applications are another embodiment of the invention.

EXAMPLES

The disclose invention is further defined in the Examples below. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt ti to various uses and conditions.

General Methods

Viscosity was measured by a Brookfield DV3T Rheometer equipped with a recirculating bath to control temperature (20° C.) and a YULA15-E(Z) spindle. The shear rate was increased using a gradient program which increased from 0.01-250 rpm and then shear rate was increased by 7.05 (1/s) every 20 seconds.

pH was measured by VWR® sympHony™ H10P.

Fibrid dimensions were measured using HiRes Fiber Quality Analyzer (OpTest Equipment, Inc., Ontario, Canada) in accordance with TAPPI T271 and ISO 16065.

Fibrid particle size were measured as a water dispersion by static light scattering using a Malvern Mastersizer 2000

Canadian Standard Freeness (CSF) was determined in accordance with ISO 5267/2 and TAPPI T227 and reported in ml.

Gurley Air Resistance of papers was measured in accordance with TAPPI T460 and reported in seconds/100 ml.

Preparation of Poly Alpha-1,3-Glucan Wet Cake and Dry Solid

U.S. Pat. No. 7,000,000 disclosed a polysaccharide fiber comprising hexose units wherein at least 50% of the hexose units within the polymer were linked via alpha-1,3-glycosidic linkages using a *Streptococcus salivarius* gtfJ enzyme. This enzyme utilizes sucrose as a substrate in a polymerization reaction producing poly alpha-1,3-glucan and fructose as end-products.

A slurry of poly alpha-1,3-glucan was prepared from an aqueous solution (0.5 L) containing *Streptococcus salivarius* gtfJ enzyme (100 unit/L) described in U.S. Patent Appl. Publ. No. 2013/0244288, which is incorporated herein by reference in its entirety, sucrose (100 g/L) obtained from OmniPur Sucrose (EM8550), potassium phosphate buffer (10 mM) obtained from Sigma Aldrich, and FERMASURE®, an antimicrobial agent, (100 ppm) obtained from DuPont adjusted to pH 5.5. The resulting enzyme reaction solution was maintained at 20-25° C. for 24 hours. A slurry was formed since the poly alpha-1,3-glucan synthesized in the reaction was aqueous insoluble. The poly alpha-1,3-glucan solids produced in the reaction were collected using a Buchner funnel fitted with a 325-mesh screen over 40 micrometer filter paper, forming the wet cake which contained about 60-80 wt % water. The poly alpha-1,3-glucan wet cake was then dried to make the dry poly alpha-1,3-glucan solid.

Examples 1a and 1b

Paper Made from Poly Alpha-1,3-Glucan Fibrids

Examples 1a and 1b were made from the poly alpha-1,3-glucan wet cake described above. Two dispersions were prepared with 10 wt % and 6 wt % poly alpha-1,3-glucan, Example 1a and 1b, respectively. The dope for Example 1a was prepared from 120 g of a 25 wt % poly alpha-1,3-glucan wet cake, 81 g of 10 wt % NaOH and 99 g of water. The dope for Example 1b was prepared from 72 g 25 wt % poly alpha-1,3-glucan wet cake, 84.6 g of 10 wt % NaOH and 143.4 g of water. The two dopes were then used to make poly alpha-1,3-glucan fibrids.

Each dope was slowly added under high shear to a blender with 200 g pH 1 aqueous sulfuric acid to precipitate the fibrids. The fibrid dispersion was then used to make papers with wood pulp. A dispersion containing 5.5 g of fibrids (on dry polymer base) (Sample A) and a dispersion containing 2.4 g of fibrids (on dry polymer based) sample (Sample B) were combined with 2 g unbleached wood pulp dispersion mixed for 3 minutes in a blender. The final slurry was poured into a 21×21 cm handsheet mold, additional water was added for total volume of 8 liters, and a wet-laid sheet or paper was formed. The fibrids had good retention during the paper making process (despite no retention aid was used). The as-made paper was easily detached from the forming wire and mass balance on the dry paper revealed that glucan was retained on the final product.

Sample B provided a yield paper weight of 3.82. A control sample having 100% cellulose was measured to be 1.85 (some of the loss relative to the loaded 2 grams is caused by moisture in the initial measured mass), hence, the paper has 1.97 grams of glucan (the expected mass from 40 grams dope loading is 2.4). With respect to material loss during sample preparation, it can be concluded that fibrillation dramatically allows glucan retention in the paper making process compared to a process that used the as made glucan or the dried form.

Also, paper made with glucan fibrids showed a decrease in paper porosity/increase in resistance to air flow. Sample A (5.6 gram paper, 1.85 unbleached pulp, 3.75 grams of glucan) gave Gurley air resistance of 29 seconds/100 ml. Sample B gave Gurley air resistance of 41 seconds/100 ml. of 3 minutes and 33 seconds. For comparison, just wood pulp paper made from the pulp had Gurley air resistance in 2-4 seconds/100 ml range.

Example 2

Physical Characterization of Poly Alpha-1,3-Glucan Fibrids

Figure 1B:

Thirteen wt % dry glucan powder was dissolved in 3.5 wt % sodium hydroxide. The dissolved glucan was prepared in the following manner: 26 grams of glucan was mixed in 113 grams of water and mixed for 2 minutes in a lab high speed blender (Waring commercial). Next, 61 grams of 10 wt % NaOH solution was slowly added while mixing rpm was adjusted to have effective recirculation and the solution is allowed to mix for a total of 3 minutes. The dope was collected within falcon tubes. In a clean blender, 200 grams of D.I. water and 2 grams of sulfuric acid were mixed and the quench solution allowed to mix at 70% of total mixer power (power input was regulated by connecting the blender to a Variac). The previously prepared dope was slowly poured (20 grams of dope in one minutes) in the agitated water/sulfuric acid mixture. A thick slurry was created with fibrid structure easily visualized in an optical microscope. In FIGS. 1a and 1b, two microscopy images of the same spot show fibrid structure. FIG. 1a shows fibrids in transmission mode (white scale bar is 50 microns). FIG. 1b shows the same spot utilizing cross polarized imaging. The bright nature of the fibrids under cross polarizers show that there is a preferential alignment of glucan molecules along the fibrid long axis. The as prepared fibrid was filtered in water with excess water until neutral pH was achieved. The thick slurry obtained this way was re-dispersed in D.I. water at 2 wt % and its viscosity measured with a Brookfield rheometer. At a shear rate of 50 1/s, a viscosity of 100 mPas (100 times more viscous than water) was measured, indicating the used of glucan fibrids as effective viscosity modifiers.

Analysis of dimensions of these fibrids using Fiber Quality Analyzer (FQA) gave such results:
Mean length:
Arithmetic—0.379 mm;
Length weighted—1.018 mm;
Weight weighted—2.124 mm
Mean width: 22.2 micrometer Example 3

Physical Characterization of Poly Alpha-1,3-Glucan Fibrids Utilizing Isopropanol as a Precipitation Solution This example used a dope prepared using similar procedures as described in Example 1. A dope was poured into a Waring high speed blender containing isopropanol as precipitation solution.

Analysis of dimensions of these fibrids using Fiber Quality Analyzer (FQA) gave the following results:
Mean length:
Arithmetic—0.182 mm;
Length weighted—0.268 mm;
Weight weighted—0.458 mm
Mean width: 23.3 micrometer Example 4

Figure 2A:
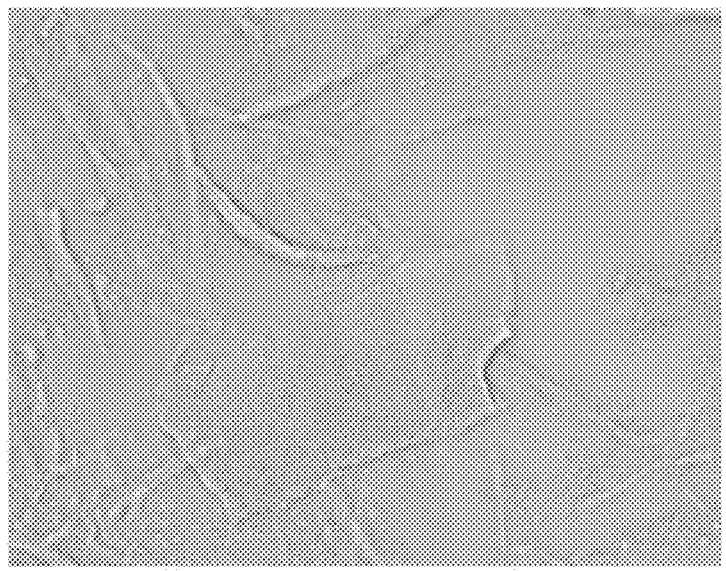
FIGS. 2a and 2b are microscopy images of the same spot showing fibrid structure.
Figure 2B:
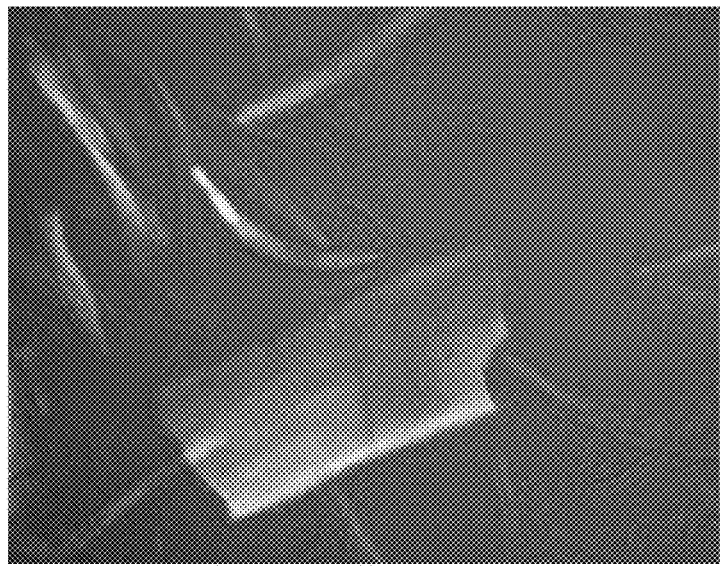

Physical Characterization of Poly Alpha-1,3-Glucan Fibrids Prepared with a Basic Quench This example used a dope prepared using similar procedures as described in Example 1 to make fibrids. In this specific case, a basic quench (200 ml of pH 10 solution) was used instead of an acidic quench. The quench solution was allowed to mix at 70% of total mixer power (power input is regulated by connecting the blender to a Variac). The previously prepared dope was slowly poured (20 grams of dope in one minute) in the agitated pH 10 solution. A thick slurry was created with fibrid structure easily visualized in an optical microscope. FIGS. 2a and 2b show microscopy images of the same spot of the fibrid. FIG. 2a shows fibrids in transmission mode (white scale bar is 50 microns). FIG. 2b is the same spot under cross polarized imaging. The bright nature of the fibrids under cross polarizers show that there is a preferential alignment of glucan molecules along the fibrid long axis. Of note is that the second quench created ribbon-like structure.

Example 5

Paper Made from the as Made, Never Dried Colloidal Glucan and Unbleached Wood Pulp Two grams of unbleached wood pulp was mixed with water using a laboratory blender for 5 minutes. Various amounts of colloidal glucan poly alpha-1,3-glucan wet cake (0.4, 4, 16, 32 and 64 grams of wet cake) were mixed with water. The glucan and wood pulp slurries were then allowed to mix together for 3 minutes before forming paper by filtration.

Paper formation with colloidal dispersion of glucan gave major glucan loss in the process. For example, when 64 grams of wet glucan (~16 grams on dry polymer basis) was formed in a paper with 2 grams of wood pulp, the final basis weight of the formed paper was at most 2.2 grams. Hence, most of the glucan was lost. Even when some glucan was retained on the formed paper (as assessed by the slight increase in basis weight of the formed paper), the porosity did not decrease significantly (1.5 seconds on a 300 cc basis for control paper, 3.5 seconds on 300 cc basis for a paper that had ~10% of glucan CD retained).

Example 6

Poly Alpha-1,3-Glucan Fibrids Made With Spherical Structures

Figure 3:
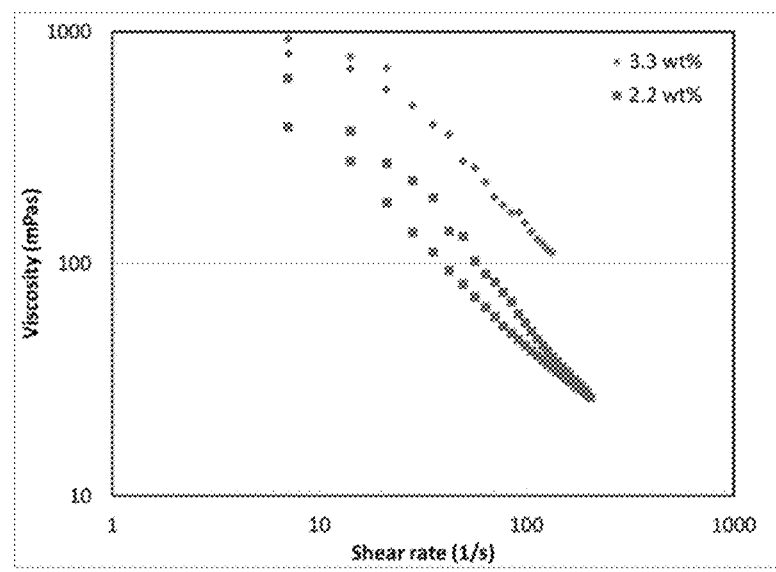
FIG. 3 is a graph showing viscosity vs. shear rate.
Figure 4:
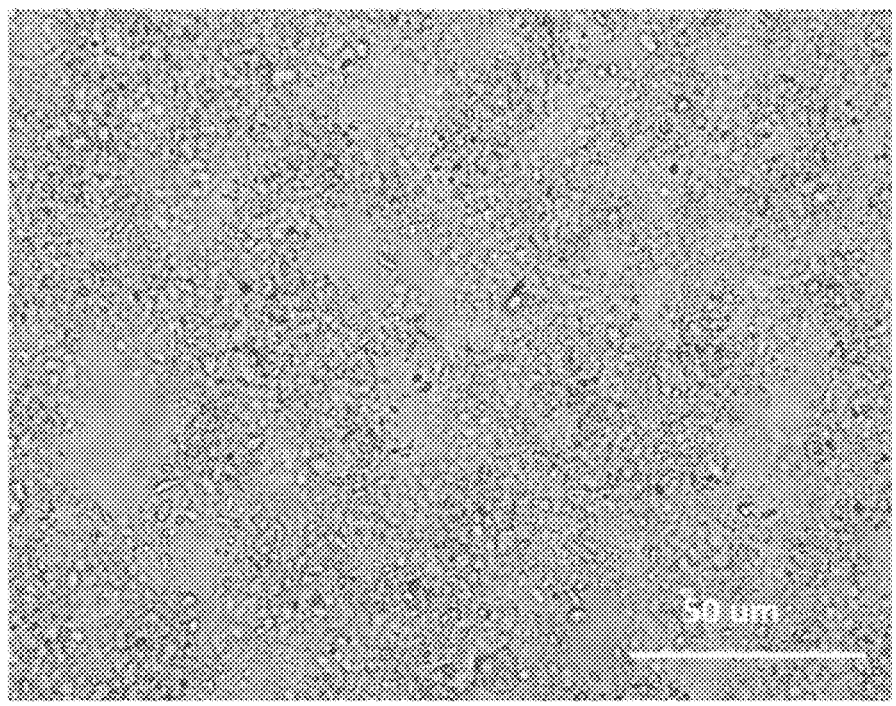
FIG. 4 is an optical microscopic image of a spherical colloidal dispersion.
Figure 5:
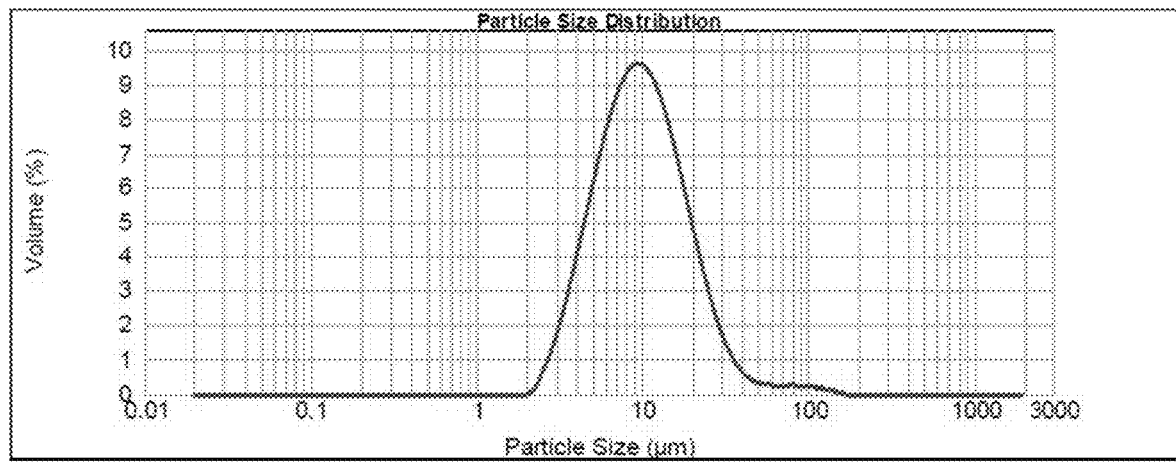
FIG. 5 shows the results from a static light measurement.

An IKA-werk ultra turrax mixer was immersed in 6 liter water. A 15 wt % glucan solution (in water with 3.8 wt % NaOH relative to total solution mass) was pumped in (50 ml/min) with a mixer agitating the solution. The solution was then pumped using a syringe pump by a 0.25 inch tubing. The tubing was placed close to the rotor stator suction hole so that the solution was subjected to high shear as soon as it entered the water quench. A total of 600 grams of dope was added in 6 liter of water. An additional 1 liter of water containing 26.39 grams of sulfuric acid (mass required to neutralize the sodium hydroxide present in the system) was then added. The obtained slurry was then filtered and washed with water to remove excess salt. The wet cake was then redispersed to a known concentration to yield the following viscosity, morphology (as characterized by optical microscopy) and particle size distribution (as characterized by light scattering). FIG. 3 shows the viscosity vs. shear rate products. Dispersion rheology was measured using a Brookfield rheometer at 20° C. The viscosity was measured by a Couette device (ULA). FIG. 4 shows an image from optical microscopy (phase contrast mode) of the spherical colloidal dispersion. Of particular interest is that most of the formed structures (that can be resolved by an optical microscope) are not elongated. FIG. 5 shows the results from a static light scattering which measures average aggregate size (measured with Malvern Mastersizer 2000). D10, D50 and D90 of this sample were 4.6, 9.6 and 21.9 microns, respectively.

Example 7

Paper Properties Made by Mixing Cellulose Pulp with Spherical Fibrids

The following composition was prepared by dissolving glucan powder: 191 grams of 10% wt % NaOH, 75 grams of polymer and 234 grams of water. The solution was than precipitated in water using a high shear rotor stator (Ultra Turrax). The solution was adjusted for pH with 10% sulfuric acid until sodium hydroxide was neutralized. Eucalyptus kraft pulp (25.8% solid) was used to make lab sheets mixed with the glucan dispersion. A retention aid was also used to improve the retention of fine particles (polyethyleneimine "Polymin HM", BASF) at 200 ppm relative to pulp mass.

Characterization of the resulting products is set forth in Table 1.

Figure 6:
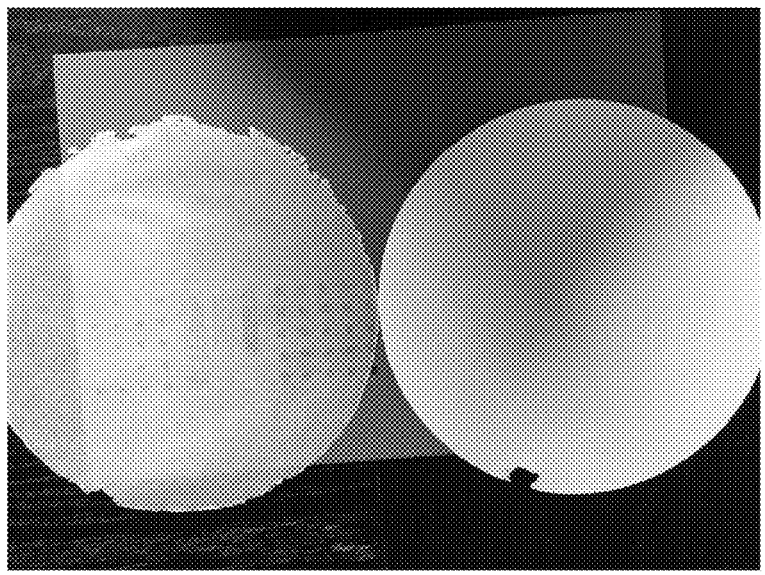
FIG. 6 shows the opacity of two paper samples. The paper on the left (Sample 7F), which contains fibrids, is transparent (low opacity), while the paper on the right (Sample 7A), which lacks fibrids, has high opacity. Refer to Example 7 and Table 1.

Interestingly, there is an overall increase in paper tensile strength, internal bond strength (Scott Bond), lower air permeability (which is associated with improved barrier properties) and increased density as the glucan fibrid concentration rises. Also, as the level of glucan fibrid increases, the paper optical properties are changed from having high opacity to have high transparency, or low opacity (see FIG. 6). In FIG. 6, Sample 7A, right, is compared to 7F, left.

TABLE 1

| Samples | Cellulose pulp wt % | glucan fibrid in wt-% | Drainage resistance (Schopper Riegler) in SR | Drainage resistance (CSF), calculated from SR in CSF | Sheet weight (23° C./ 50% RH) in g (climatised) | Thickness in μm | Apparent density in g/cm³ | Scott-Bond (z-Strength) in J/m² | Air permeability (Gurley) in sec/100 cm³ |
|---|---|---|---|---|---|---|---|---|---|
| 7A | 100.0% | 0.0% | 27 | 475 | 2.51 | 131 | 0.61 | 432 | 7 |
| 7B | 100.0% | 0.0% | 28 | 450 | 2.45 | 127 | 0.61 | 380 | 7 |
| 7C | 99.3% | 0.7% | 30 | 430 | 2.35 | 121 | 0.61 | 413 | 7 |
| 7D | 94.0% | 6.0% | 45 | 265 | 2.10 | 105 | 0.63 | 502 | 11 |
| 7E | 86.6% | 13.4% | 80 | 20 | 1.64 | 77 | 0.67 | 658 | 45 |
| 7F | 65.3% | 34.7% | 88 | — | 2.32 | 76 | 0.96 | 1000 | |

| Samples | Tensile index in Nm/g | Breaking elongation in % | Tensile energy absorption in J/m² | Tensile stiffness in kN/m | Young's modulus in GPa | Reflectance (R457 D65) in % | Opacity (C C/2) in % |
|---|---|---|---|---|---|---|---|
| 7A | 43.5 | 3.33 | 87.1 | 458 | 3.51 | 88.1 | 83.0 |
| 7B | 42.1 | 3.05 | 76.2 | 435 | 3.42 | 88.8 | 81.9 |
| 7C | 44.9 | 3.47 | 87.0 | 414 | 3.43 | 88.8 | 80.7 |

TABLE 1-continued

| | | | | | | | |
|---|---|---|---|---|---|---|---|
| 7D | 49.6 | 3.93 | 96.2 | 377 | 3.59 | 88.3 | 76.9 |
| 7E | 52.9 | 3.35 | 67.7 | 296 | 3.85 | 85.3 | 65.9 |
| 7F | 54.5 | 1.20 | 28.7 | 494 | 6.54 | 82.2 | 27.6 |

Example 8

Surface Charge Modification of Poly Alpha-1,3-Glucan Fibrids

A 12 wt % glucan polymer was dissolved in 4.2 wt % NaOH (relative to total dope mass) and was mixed. In half of the sample (250 grams of solution) was added 11 grams of 60% 3-chloro-2-hydroxypropyl-trimethylammonium chloride in water. The solution containing 3-chloro-2-hydroxypropyl-trimethylammonium chloride was mixed for few more minutes to allow homogeneous dispersion of the reagent and left static overnight for the reaction to complete. Next, 230 grams of the dissolved polymer was then quenched in 2 liters of water (see example 6 for specific equipment used) and neutralized with 100 grams, 10 wt % sulfuric acid solution. Two samples were made: Sample A: reference material with no 3-chloro-2-hydroxypropyl-trimethylammonium chloride and Sample B: 6.6 grams of 3-chloro-2-hydroxypropyl-trimethylammonium chloride and 30 grams of glucan polymer.

Figure 7:
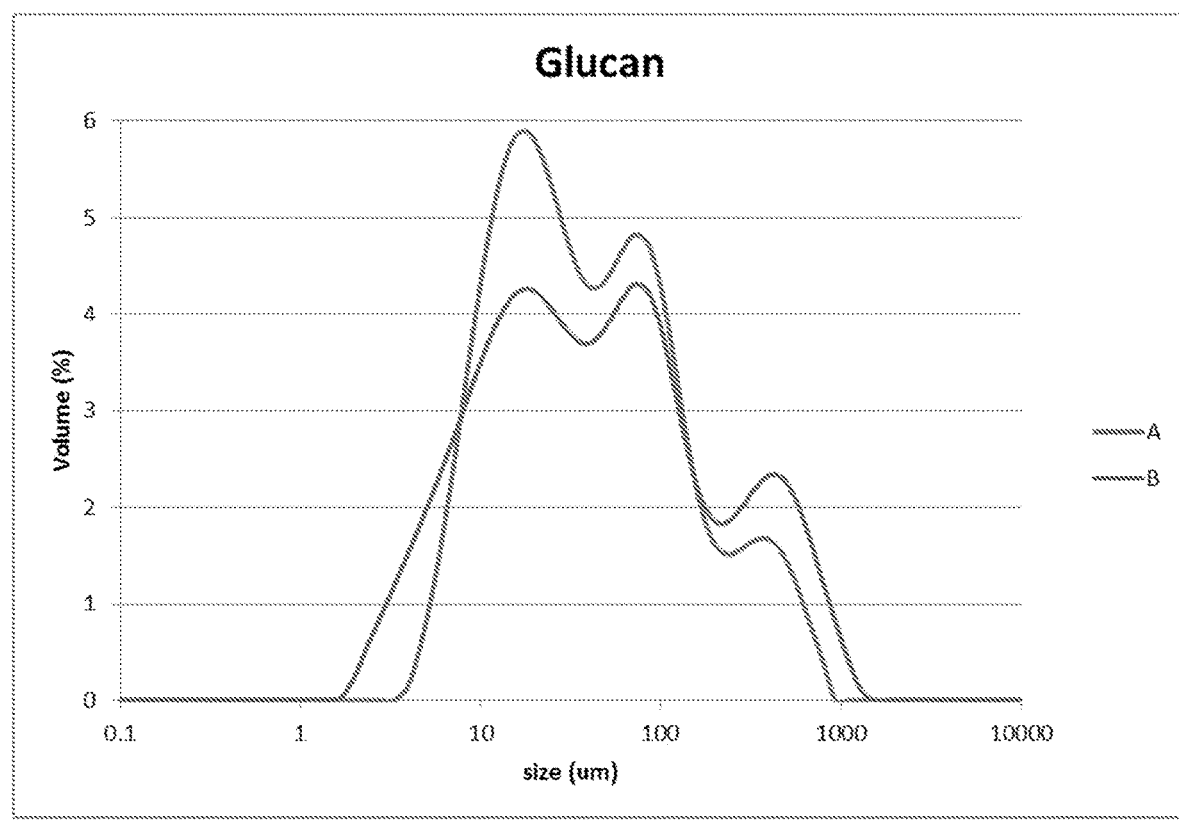
FIGS. 7 and 8 are graphs further characterizing two samples, one having a mostly neutral surface and the other having a positive surface.
Figure 8:
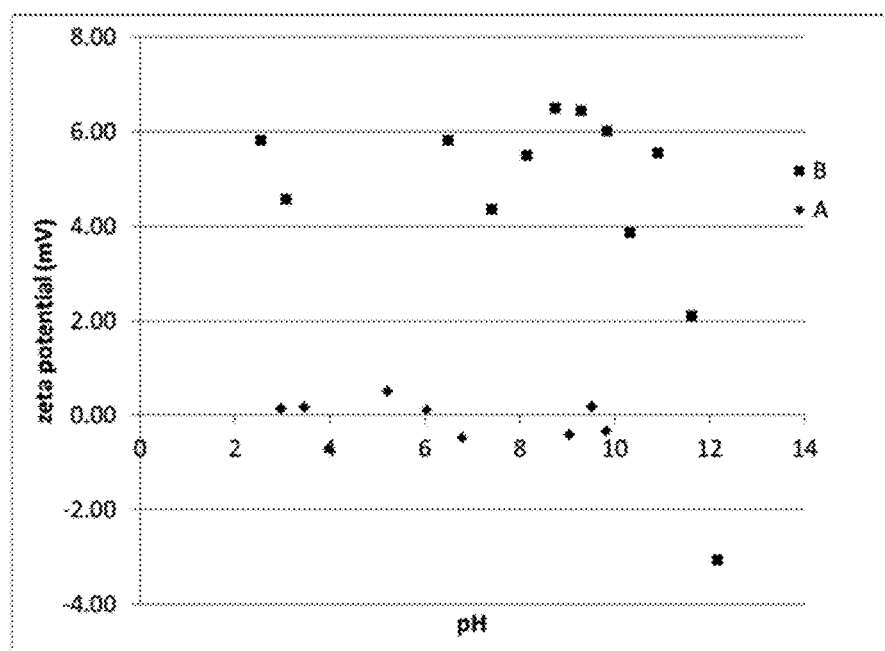

FIGS. 7 and 8 represent characterization of the two samples. Note how the two samples have comparable particle size distribution. However, the two samples have distinctively different surface charge. Specifically, sample A has very low zeta potential with no-distinct isoelectric point. Sample B has an order of magnitude higher zeta potential and a clear cross over from positive to negative values for the zeta potential. This indicates that sample B has a positive surface charge while sample A has a mostly neutral surface. Excess water from Sample A was easily filtered by using a cellulose-paper filter (~tens of minutes). Using the same set-up and filter, excess water could not be removed from sample B by vacuum filtration after 24 hours. This indicates the affinity of sample B to cellulose surface, a particularly desired feature in paper making to improve fine cellulose flocculation and overall paper strength improvement.

What is claimed is:

1. Fibrids comprising poly alpha-1,3-glucan or surface charge-modified poly alpha-1,3-glucan.

2. The fibrids of claim 1, wherein the fibrids have a fibrous shape with an average length of between 100 nm and 10 mm and width of between 10 nm and 200 µm.

3. A paper comprising:
(a) the fibrids of claim 1; and
(b) optionally, wood pulp.

4. The paper of claim 3, wherein the paper is in the form of a packaging material or an insulating material.

5. A process for making a paper, said method comprising:
(a) dispersing the fibrids of claim 1, optionally with wood pulp, in an aqueous medium to form a slurry; and
(b) forming a paper from the slurry by filtering off the aqueous medium to form a wet paper and then drying the wet paper.

6. The process of claim 5, further comprising:
(c) calendering the paper.

7. A viscosity modifier comprising the fibrids of claim 1.

8. An emulsifier comprising the fibrids of claim 1.

9. The fibrids of claim 1, wherein the fibrids comprise the poly alpha-1,3-glucan.

10. The fibrids of claim 1, wherein the fibrids comprise the surface charge-modified poly alpha-1,3-glucan.

11. The fibrids of claim 10, wherein the surface charge-modified poly alpha-1,3-glucan has a positive surface charge.

12. The fibrids of claim 11, wherein the surface charge-modified poly alpha-1,3-glucan is obtained by reaction of 3-chloro-2-hydroxypropyl-trimethylammonium chloride with poly alpha-1,3-glucan.

13. The fibrids of claim 10, wherein the surface charge-modified poly alpha-1,3-glucan has a zeta potential that is higher than the zeta potential of unmodified poly alpha-1,3-glucan.

14. The fibrids of claim 1, wherein the fibrids are comprised in an emulsifier or a viscosity modifier.

15. The fibrids of claim 1, wherein at least 50% of the glycosidic linkages of the poly alpha-1,3-glucan and the surface charge-modified poly alpha-1,3-glucan are alpha-1,3-glycosidic linkages.

16. The fibrids of claim 15, wherein at least 90% of the glycosidic linkages of the poly alpha-1,3-glucan and the surface charge-modified poly alpha-1,3-glucan are alpha-1,3-glycosidic linkages.

17. A process for making fibrids, said method comprising precipitating poly alpha-1,3-glucan or surface charge-modified poly alpha-1,3-glucan under shear in a non-solvent to produce a suspension comprising fibrids.

18. The process of claim 17, wherein at least one of (i) viscosity of the suspension containing the fibrids, (ii) size of the fibrids, or (iii) shape of the fibrids is controlled by altering at least one process parameter wherein the process parameter is the dope concentration, the type of mixer, the mixing speed, the pH of precipitation bath, the rate of addition of solvent in which the glucan is dissolved, the amount of non-solvent used, the duration of mixing, the rate of neutralization, and/or the concentration of neutralizer.

19. A process for making fibrids, said method comprising:
(a) dissolving poly alpha-1,3-glucan or surface charge-modified poly alpha-1,3-glucan in a solvent to make a glucan solution;
(b) precipitating poly alpha-1,3-glucan or surface charge-modified poly alpha-1,3-glucan under shear to produce a suspension containing the fibrids.

20. The process of claim 19, wherein the fibrid-containing suspension of step (b) is filtered to isolate the fibrids.

21. The process of claim 20, wherein the isolated fibrids are dried.

22. The process of claim 19, wherein the process includes at least one of the following:
(i) the solvent can be an aqueous basic solution; and
(ii) the precipitation of (b) comprises at least one of an aqueous acidic solution and/or an alcohol.

23. A process for making surface charge-modified poly alpha-1,3-glucan fibrids, said method comprising:
(a) contacting poly alpha-1,3-glucan with 3-chloro-2-hydroxypropyl trimethylammonium chloride to obtain surface charge-modified poly alpha-1,3-glucan; and
(b) precipitating the surface charge-modified poly alpha-1,3-glucan under shear in a non-solvent to produce a suspension comprising surface charge-modified poly alpha-1,3-glucan fibrids.

* * * * *